United States Patent [19]
Krawczyk et al.

[11] Patent Number: 5,523,508
[45] Date of Patent: Jun. 4, 1996

[54] PROCESS FOR LINEAR ALPHA-OLEFIN PRODUCTION: ELIMINATING WAX PRECIPITATION

[75] Inventors: Mark A. Krawczyk, Chicago; Richard E. Marinangeli; R. Joe Lawson, both of Arlington Heights, all of Ill.

[73] Assignee: UOP, Des Plaines, Ill.

[21] Appl. No.: 366,153

[22] Filed: Dec. 29, 1994

[51] Int. Cl.⁶ .................................................. C07C 2/24
[52] U.S. Cl. .................. 585/523; 585/315; 585/316; 585/329; 585/522; 585/526; 585/527
[58] Field of Search .................................. 585/315, 316, 585/329, 522, 523, 526, 527

[56] References Cited

U.S. PATENT DOCUMENTS

| | | | |
|---|---|---|---|
| 3,641,191 | 2/1972 | Fernald et al. | 260/683.150 |
| 4,547,612 | 10/1985 | Tabak | 585/533 |
| 4,668,823 | 5/1987 | Murray | 568/17 |
| 4,689,437 | 8/1987 | Murray | 585/526 |
| 4,716,138 | 12/1987 | Murray | 502/117 |
| 4,822,915 | 4/1989 | Murray | 568/13 |
| 4,879,428 | 11/1989 | Harandi et al. | 585/533 |

OTHER PUBLICATIONS

Ullman's Encyclopedia of Industrial Chemistry, 5th Ed., V. A13, pp. 245 et. ff., VCH (1989). (month unknown).

*Primary Examiner*—Shrive Beck
*Assistant Examiner*—Timothy H. Meeks
*Attorney, Agent, or Firm*—Thomas K. McBride; Eugene I. Snyder

[57] ABSTRACT

Linear alpha-olefin formation via oligomerization of ethylene using transition metal catalysis leads to a Schultz-Flory distribution of oligomers. At modest temperatures formation of heavy oligomers which are waxy solids only partly soluble in the LAO product mix causes reactor plugging and curtailing the time of continuous runs. Recycling a portion of a lighter oligomeric fraction obviates this problem and permits runs uninterrupted by solids formation.

10 Claims, 1 Drawing Sheet

PROCESS FOR LINEAR ALPHA-OLEFIN PRODUCTION: ELIMINATING WAX PRECIPITATION

BACKGROUND OF THE INVENTION

Linear olefins are one of the most useful classes of hydrocarbons used as raw materials in the petrochemical industry and among these the linear alpha-olefins—unbranched olefins whose double bond is located at a terminus of the chain—form an important subclass. Linear alpha-olefins can be converted to linear primary alcohols by hydroformylation (oxo synthesis); alcohols of carbon number less than eleven are used in the synthesis of plasticizers whereas those of carbon number greater than eleven are used in the synthesis of detergents. Hydroformylation also can be used to prepare aldehydes as the major products which in turn can be oxidized to afford synthetic fatty acids, especially those with an odd carbon number, useful in the production of lubricants. Linear alpha-olefins also are used in the most important class of detergents for domestic use, namely the linear alkylbenzenesulfonates, which are prepared by Friedel-Crafts reaction of benzene with linear olefins followed by sulfonation.

Another important utilization of alpha-olefins is radical hydrobromination to give primary bromoalkanes which are important intermediates in the production of thiols, amines, amine oxides, and ammonium compounds. Direct sulfonation of the alpha-olefins afford the alpha-olefin sulfonates, a mixture of isomeric alkenesulfonic acids and alkanesulfones, which are effective laundry agents even in hard water and at low concentrations. Linear alpha-olefins, particularly those of eight carbons and under also are used as comonomers in the production of high density polyethylene and linear low density polyethylene.

Although linear olefins are the product of dehydrogenation of linear alkanes, the major portion of such products consists of the internal olefins. Preparation of alpha-olefins is based largely on oligomerization of ethylene, which has as a corollary that the alpha-olefins produced have an even number of carbon atoms. Oligomerization processes for ethylene are based mainly on organoaluminum compounds or transition metals as catalyst. Using catalytic quantities of, for example, triethylaluminum, the oligomerization of ethylene proceeds at temperatures under 200° C. to afford a mixture of alpha-olefins whose carbon number follows a Schultz-Flory distribution. In the C6–C10 range there is less than 4% branched alpha-olefins, but the degree of branching increases to about 8% as the chain length is extended to 18. A modified process, the so-called Ethyl process, affords a high conversion of ethylene to alpha-olefins with a more controlled distribution but product quality suffers dramatically, particularly in the content of branched olefins. Thus, in the C14–C16 range linear alpha-olefins represent only about 76% of the product.

A notable advance in the art accompanied the use of transition metals as catalysts for ethylene oligomerization. The use of, for example, nickel, cobalt, titanium, or zirconium catalysts afforded virtually 100% monoolefins with greater than 97% as alpha-olefins, under 2.5% as branched olefins, and under 2.5% as internal olefins. Since the catalysts are insoluble in hydrocarbons, oligomerization by catalyst systems based on transition metals typically is performed in a polar solvent to solubilize the catalyst. Ethylene and its oligomers have limited solubility in the polar solvents used, consequently the oligomerization process is associated with a 3-phase system; a polar liquid solvent phase containing the catalyst, a second liquid hydrocarbon phase (consisting of the oligomers produced), immiscible with the polar liquid phase, and ethylene in the vapor phase. Such a system permits of a continuous oligomerization process, since ethylene can be introduced into the polar phase and oligomerization products can be withdrawn as the hydrocarbon phase.

Ethylene oligomerization affords alpha-olefins with a Schultz-Flory distribution which is catalyst dependent and, at least for the catalysts of major interest herein, temperature dependent to only a minor degree. Murray recently has described a class of catalysts having a transition metal component particularly attractive as oligomerization catalysts; U.S. Pat. No. 4,689,437, U.S. Pat. No. 4,716,138, and U.S. Pat. No. 4,822,915. See also U.S. Pat. No. 4,668,823. Using such catalysts under conditions where the Schultz-Flory distribution constant is about 0.65 affords an oligomerization product whose alpha-olefin distribution in the C6–C16 range is particularly desirable from an economic viewpoint. That is, the economic value of ethylene oligomers may be maximized by having a Schultz-Flory distribution of about 0.65. A concomitant of oligomerization at such conditions is the production of about 10% of oligomers having 20 or more carbon atoms (C20+) which are solids at ambient temperature, and therein lies the problem whose solution is our invention.

The C20+ oligomers have limited solubility in the hydrocarbon phase of the oligomerization process described above, hence tend to separate as waxy solids. The oligomerization process then becomes a four-phase system; a vapor phase of ethylene, a polar solvent phase with dissolved catalyst, an immiscible liquid hydrocarbon phase, and a solid phase (wax) of C20+. The formation of solids tends to plug the reactor as currently configured, so a continuous process becomes interrupted periodically due to the necessity of unplugging the reactor, and even during process operation liquid flow is impeded as solids build. We have solved this problem by recycling a portion of the lighter oligomers, viz., the C12–C18 oligomers, to the reactor in order to solubilize the C20+ formed and avoid plugging. In outline form our process is the formation of ethylene oligomers with the desired Schultz-Flory distribution, especially one near 0.65, separating and recovering the C6–C10 oligomers, separating the C20+ solids, separating and recovering the C12–C18 oligomers substantially free of C20+, and recycling a portion of the C12–C18 fraction sufficient to maintain a homogeneous hydrocarbon phase in the reactor. Thus, the recycled C12–C18 acts as a solvent for the C20+ oligomers.

Although the foregoing is an important variant it is only representative of a much larger class. In general, oligomerization of ethylene governed by a Schulz-Flory distribution will give heavy oligomers, i.e., oligomers of sufficiently high carbon number that they are waxy solids only partly soluble in the oligomeric product mix under oligomerization process conditions. These solids will be a problem in causing reactor plugging, and prevention of solid separation is highly desirable. This can be effected by increasing the solubility of the heavy oligomers in the liquid hydrocarbon phase by recycling some of the lighter oligomer fractions to the hydrocarbon phase, with the exact composition of the recycled phase quite dependent upon the carbon number of the heavy oligomers separating as a waxy solid, the oligomerization process temperature, the amount of recycle which can be tolerated or which is desirable, the nature of the fractionating process, and so forth. But in all events a lighter fraction is recycled to solubilize the heavy oligomers and thereby avoid plugging. The case described in the foregoing paragraph then becomes a specific embodiment of our more general invention.

SUMMARY OF THE INVENTION

The purpose of our invention is the preparation of linear alpha-olefins from the oligomerization of ethylene using as a catalyst a solution of a transition metal catalyst system in a polar solvent without accompanying separation of heavy oligomers as solids in the oligomeric hydrocarbon phase. A broad embodiment comprises returning a portion, substantially free of heavy oligomers which would be solid at process temperatures, of a lighter oligomeric fraction to the oligomerization reactor, the portion being sufficient to solubilize the heavy oligomers. A specific embodiment comprises returning a portion, substantially free of C20+ (i.e., having less than about 1% C20+ ), of oligomers in the C12–C18 range to the oligomeric hydrocarbon phase in the oligomerization reactor. In a more specific embodiment the transition metal catalyst system is Ni (II) salt, an organophosphorus sulfonate, and a hydride donor. In another specific embodiment the oligomerization is conducted at conditions to afford a Schultz-Flory distribution between about 0.5 to about 0.8. In yet another embodiment the polar solvent used is sulfolane. Other embodiments will be apparent from our ensuing description.

DETAILED DESCRIPTION OF THE INVENTION

Figure 1:
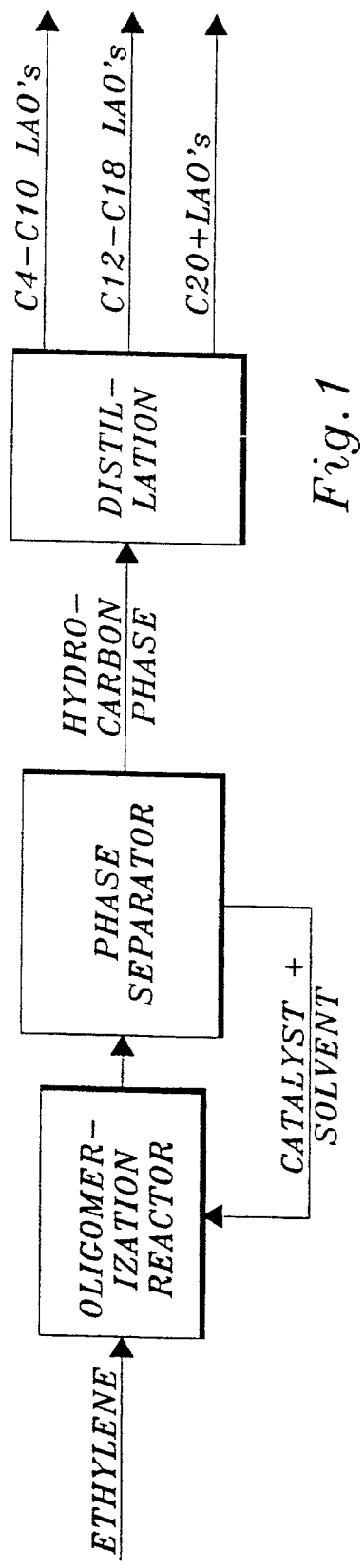
FIG. 1 is a process flow diagram representative of LAO production according to the prior art.

The oligomerization of ethylene using a solution of a transition metal catalyst system in a polar solvent proceeds with the formation of a separate hydrocarbon phase consisting largely of linear alpha-olefins formed according to the Schultz-Flory distribution. At a Schultz-Flory distribution constant of greater than about 0.60 considerable amounts of C20+ oligomers are formed which are not completely soluble in the hydrocarbon (and polar solvent) phase at process temperatures. We refer to these as heavy oligomers, for they are C20+ oligomeric products. The solids which separate tend to clog the reactor, thus interfering with a continuous process, which is the preferred mode for ethylene oligomerization. Since a Schultz-Flory distribution constant greater than about 0.50 affords an economically beneficial distribution of linear alpha-olefins containing fewer than 20 carbons, there is a need to maintain homogeneity in the hydrocarbon phase. We have succeeded in solving this problem by recycling the portion of a lighter oligomeric fraction, e.g., the C12–C18 oligomers, to the hydrocarbon phase, effectively solubilizing the C20+ oligomers therein and preventing a solid phase from forming without significantly affecting the amount of C20+ formed.

The process of our invention deals with the oligomerization of ethylene as catalyzed by transition metal catalyst systems. See, for example, Ullman's Encyclopedia of Industrial Chemistry, 5th Ed., V. A13, pp. 245 et. ff., VCH (1989). A particularly desirable transition metal catalyst system is that described by Murray in U.S. Pat. No. 4,689,437, all of which is incorporated herein. The transition metal catalyst system described there is a reaction product of three components; a transition metal compound, a catalyst activator, and an organophosphorus sulfonate ligand. Other transition metal catalyst systems are described in, e.g., U.S. Pat. Nos. 3,635,937, 3,637,636, 3,644,563, 3,644,564, 3,647,915, 3,661,803 and 3,686,159. Since transition metal catalyst systems for ethylene oligomerization are well known in the art they need not be further discussed herein.

The oligomerization of ethylene is a liquid phase reaction, and the catalyst can be either dissolved in a solvent or suspended in a liquid medium. The solvent or liquid medium of course needs to be inert to process components and apparatus under process conditions. Examples of solvents include ethanol, methanol, water, sulfolane (tetramethylenesulfone), ethylene glycol, 1,4-butanediol, ethylene carbonate, as well as mixtures of the foregoing. In the variant under discussion here solvents which permit ready phase separation from oligomeric products are preferred in order to have a polar solvent phase and a hydrocarbon phase. The most preferred solvent for ethylene oligomerization is sulfolane in which the catalysts of our invention are quite soluble but the oligomers are not.

Typical catalyst concentrations are in the range of about 10 ppm to about 1,000 ppm of transition metal. Some of the more active catalysts give quite high reaction rates at 40 ppm, and a broader range of catalyst concentration is between about 0.1 to about 1,000 ppm. In a preferred mode of practicing our invention catalyst concentrations range between about 15 and about 300 ppm.

Oligomerization conditions include a temperature in the range of about 5° C. to about 200° C., with the interval between 20° and 140° C. preferred and that between 30° and about 80° C. even more usual. The process can be run at pressures in the range of about atmospheric pressure to about 5,000 psig, although preferred pressures are in the range of about 400 to about 2,000 psig. These pressures are the pressures at which the ethylene is introduced into the reactor and at which the reactor is maintained.

As commented on above, the oligomerization process forms oligomers which are predominantly linear alpha-olefins having from 4 to over 20 carbon atoms and which have low solubility in the polar solvents utilized, especially where sulfolane is the solvent for the transition metal catalyst systems of our invention. Consequently, oligomer formation is accompanied by formation of a separate hydrocarbon phase, at least a portion of which is continually removed. The constituents of this hydrocarbon phase are ethylene oligomers whose relative proportions closely follow a Schultz-Flory distribution. The practice of this invention is particularly pertinent to those cases where substantial amounts of heavy oligomers are formed, which is a function of the Schultz-Flory distribution. By "heavy oligomers" is meant oligomers normally a (waxy) solid at process temperatures, and may be considered as C20+ oligomers. These heavy oligomers have a limited, temperature-dependent solubility in the hydrocarbon phase. But since the temperature also affects oligomer product quality via the selectivity to linear alpha-olefins, it is not practical to raise the reaction temperature in order to maintain homogeneity. Unless homogeneity in the hydrocarbon phase is maintained, reactor (or an ancillary unit) clogging results, which is precisely the problem to which our invention is directed.

Figure 2:
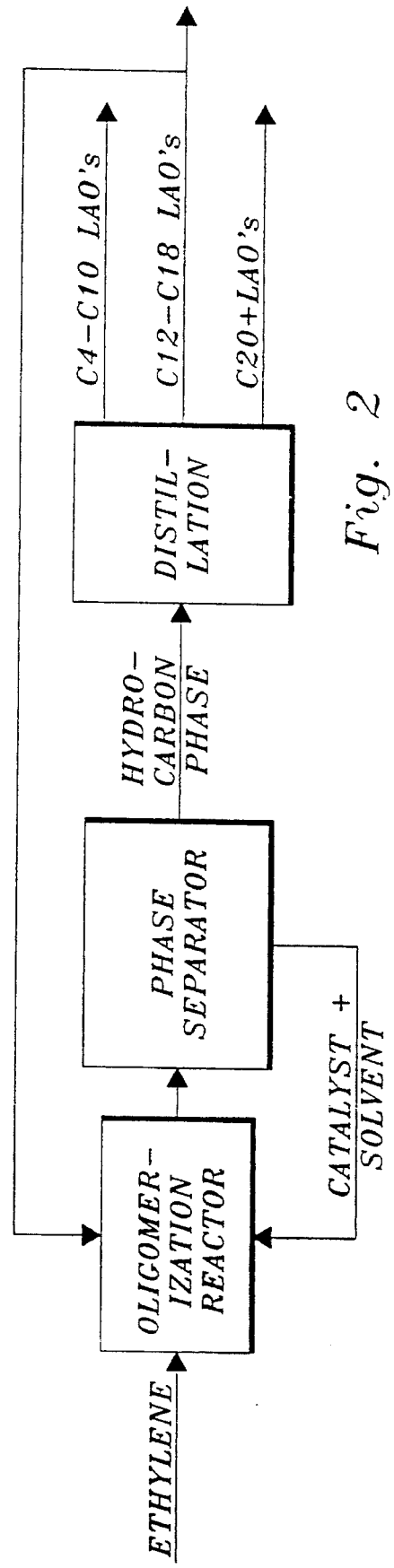
FIG. 2 is a process flow diagram representative of LAO production according to our invention.

In a typical prior art ethylene oligomerization process diverse oligomer cuts are obtained, such as by distillation, e.g., one fraction containing largely C4–C10 linear alpha-olefins, a second fraction containing C12–C18 linear alpha-olefins, and another fraction of oligomers of 20 or more carbon atoms. This is shown schematically in FIG. 1 as representative of the prior art. In contrast to this is our FIG. 2, which represents an embodiment of the instant invention. In particular, although the same three oligomer fractions may be obtained, a portion of the fighter oligomers, i.e., C4–C18, substantially free of C20+ oligomers, is recycled to the reactor in order to maintain homogeneity in the hydrocarbon phase, i.e., to solubilize the heavy oligomers. By "substantially free of C20+ oligomers" is meant that less than 1 weight percent of those oligomers which are solids at the process temperature is present. In a preferred mode only the C10–C18 oligomers are recycled; in a more preferred mode it is the C12–C18 oligomers which are recycled. In a somewhat more preferred mode only the C12–C16 oligomers are recycled. Since the recycled lighter oligomers, such as C12–C18, are not in the sulfolane phase, little (if any) additional heavy oligomers form with recycling. The amount of lighter oligomers such as C12–C18 (or C12–C16, whatever the recycling stream contains) recycled needs to be sufficient to be effective in maintaining a homogeneous hydrocarbon phase, i.e., effective to prevent wax formation by precipitation of heavy oligomers in the hydrocarbon phase. This is the sole applicable criterion as to the amount of the light oligomer recycle stream; larger amounts clearly may be used in the practice of our invention, although recycle of the minimum amount effective to maintain homogeneity in the hydrocarbon phase is favored for economic reasons.

From the foregoing it ought to be clear that the amount of the recycle stream needs to be determined for the particular oligomerization conditions practiced. So, for example, our invention is applicable to oligomerization having a Schultz-Flory distribution of at least 0.60, with oligomerizations having a Schultz-Flory distribution between about 0.60 and about 0.80, and especially between 0.60 and 0.75, particularly pertinent in the practice of our invention. In the case of an oligomerization with a Schultz-Flory distribution constant of about 0.65, which affords approximately 10 weight percent C20 + oligomers, good results are observed when sufficient C12–C18 is recycled so that the hydrocarbon phase contains about 25 weight percent of C12–C18. Since the C12–C18 oligomers in the reaction product amount to only about 16% of the total, it is clear that at startup there may be total recycle of the C12–C18 fraction until the desired steady state amount has been reached.

The process of our invention is practiced in a way typical for ethylene oligomerization other than the addition of a recycle stream. Thus, ethylene is continually fed to a reactor sufficient to maintain ethylene pressures between about 400 and about 5,000 psig at temperatures between about 0° and 200° C. The transition metal catalyst system is present in solution in a polar solvent, preferably sulfolane. Oligomerization proceeds with formation of a separate hydrocarbon phase resulting from the low solubility of oligomers in the sulfolane. The hydrocarbon phase is continually removed and separated, as by distillation, into several streams. In particular, a fraction of e.g., C12–C18 oligomers is recovered which is substantially free of heavy oligomers. A portion of this oligomer fraction is recycled to the reactor in an amount effective to maintain homogeneity in the hydrocarbon phase. The amount recycled will be dependent upon the Schultz-Flory distribution, which determines the relative amount of heavy oligomers formed, as well as the temperature, which influences the solubility of the heavy oligomers in the hydrocarbon phase.

Our invention as summarized and described in the prior paragraph also lends itself to a still more general description, which is particularly relevant to LAO production from ethylene oligomerization at temperatures over 65° C., especially in the range of 65° up to 100° C. Such a process will likely produce heavy oligomers which are solid at process temperatures, and induce reactor plugging, curtailing run times of continuous LAO production. The heavy oligomers contain at least 2n carbon atoms, where n is an integer at least about 15 and may be as high as about 25. Clogging is obviated by recycling to the liquid hydrocarbon phase a lighter oligomeric fraction containing no more than about 1% total of heavy oligomers, i.e., all oligomers solid at process temperatures. The lighter oligomers are those containing from 4 up to about 2(n−1) carbon atoms, and the recycled light oligomer stream contains no more than 1 weight percent of oligomers containing at least n carbon atoms.

The following examples are merely illustrative of our invention, and do not limit it in any way.

EXAMPLES

A continuous reactor system consisted of a stirred autoclave, containing a solution of sulfolane and catalyst, and a separator. Ethylene was supplied to the reactor at a rate of 160 g/hr at 1500 psig. A mixture of the sulfolane solution, oligomeric product, and unreacted ethylene was conducted from the reactor via a second line to a separator; the sulfolane solution of catalyst was recycled to the reactor, and the product/ethylene mixture was drawn off.

The catalyst solution was prepared by adding 1 part by weight of the sodium salt of diphenyl(2-naphthyl-1-sulfonic acid)phosphine and 2 parts nickel tetrafluoroborate in sulfolane at a total nickel concentration of about 25 ppm Ni. An activator solution of $NaBH_4$ was then added at a ratio of 1 part borohydride to 2 parts nickel. Additional ligand, nickel salt, and activator were added in a 1:2:1 proportion by weight to ensure ethylene conversions in the 10–50 weight percent range. Reactions were conducted at 60° C.

Using the foregoing procedure oligomerization runs generally were terminated due to plugging of the reactor system by wax. In particular, wax deposits were formed in the line between the reactor outlet and the separator, in the catalyst recycle line, at the point where the catalyst recycle and the fresh catalyst/activator lines joined, and in the product withdrawal line. The longest run which could be conducted before shutdown due to wax plugging lasted for 388 hours; the shortest plugging time was 80 hours.

Following these runs, the plant was modified so that tetradecene (as model for the C12–C16 oligomer fraction) could be added directly into the autoclave. The tetradecene was removed from the autoclave with the LAO product. A series of 7 runs were conducted with a tetradecene feed rate of 20 g/hr. None of these runs was shut down due to plugging; two runs of longer than 500 hours were completed, and these runs were shut down by choice when experimental objectives were attained. Some results are summarized in the accompanying table.

TABLE 1

Effect of Simulated Recycle on Plugging

| Run | HOS[a] (hr) | C14 Rate[b] (g/hr) | LAO Product Formation Rate (g/hr) | Ethylene Conversion (wt %) | Percentage added C14 in product[c] | Plugging |
|-----|------|------|------|------|----|-----|
| A | 80 |  | 33.9 | 21.2 | 0 | yes |
| B | 388 |  | 70.0 | 43.8 | 0 | yes |
| C | 252 |  | 78.8 | 49.3 | 0 | yes |
| C | 55 | 19.9 | 60.3 | 37.7 | 25 | no |
| D | 544 | 19.2 | 37.5 | 23.4 | 34 | no |
| E | 498 | 20.4 | 54.9 | 34.3 | 27 | no |

[a]Hours on stream
[b]Rate of addition of tetradecene
[c]That is, $100 \times C14/(C14 + LAO)$

What is claimed is:

1. A process for continuous oligomerization of ethylene to form linear alpha-olefins using a transition metal catalyst system comprising:
   a. introducing ethylene at oligomerization conditions into a polar phase consisting essentially of a solution of the transition metal catalyst system in a polar solvent;
   b. oligomerizing ethylene in said polar phase to afford oligomers having from 4 to more than 20 carbon atoms, said oligomers consisting essentially of linear alpha-olefins and forming a hydrocarbon phase separate from said polar phase;
   c. continually withdrawing said hydrocarbon phase and separating therefrom C4–C 18 oligomers substantially free of C20+ oligomers; and
   d. returning to the hydrocarbon phase a portion of the C4–C18 oligomers in an amount sufficient to maintain homogeneity in said hydrocarbon phase.

2. The process of claim 1 where the C4–C18 oligomers returned to the hydrocarbon phase contain no more than about 1 weight percent C20+ oligomers.

3. The process of claim 1 where the oligomers returned to the hydrocarbon phase have from 10 up to about 18 carbon atoms.

4. The process of claim 3 where the oligomers returned to the hydrocarbon phase have from 12 up to about 18 carbon atoms.

5. The process of claim 4 where the oligomers returned to the hydrocarbon phase have from 12 up to about 16 carbon atoms.

6. The process of claim 1 where the transition metal catalyst system comprises a transition metal compound, an organophosphorus sulfonate ligand, and optionally a catalyst activator.

7. The process of claim 1 where the polar solvent is selected from the group consisting of ethanol, methanol, sulfolane, ethylene glycol, 1,4-butanediol, and ethylene carbonate.

8. The process of claim 7 where the polar solvent is sulfolane.

9. The process of claim 1 where the oligomerization conditions include a temperature from about 5° to about 200° C. and a pressure between about atmospheric to about 5,000 psig.

10. A process for continuous oligomerization of ethylene to form linear alpha-olefins using a transition metal catalyst system comprising:
   a. introducing ethylene at an oligomerization temperature from about 65 ° to about 100° C. into a polar phase consisting essentially of a solution of the transition metal catalyst system in a polar solvent;
   b. oligomerizing ethylene in said polar phase to afford oligomers consisting essentially of linear alpha-olefins, said oligomers forming a hydrocarbon phase separate from said polar phase, said hydrocarbon phase containing i) heavy oligomers normally solid at the oligomerization temperatures and having at least 2n carbon atoms, and ii) lighter oligomers having no more than 2(n−1) carbon atoms, where n is an integer from about 15 up to about 20;
   c. continually withdrawing said hydrocarbon phase and separating therefrom the lighter oligomers substantially free of the heavy oligomers; and
   d. returning to the hydrocarbon phase a portion of the lighter oligomers in an amount sufficient to maintain the heavy oligomers in solution in said hydrocarbon phase.

* * * * *